United States Patent
Leiboff et al.

(10) Patent No.: US 11,189,813 B2
(45) Date of Patent: Nov. 30, 2021

(54) WOUND MANAGEMENT METHOD AND APPARATUS

(71) Applicant: Arnold R Leiboff, Old Field, NY (US)

(72) Inventors: Arnold R Leiboff, Old Field, NY (US); Jooli Han, Pittsburgh, PA (US)

(73) Assignee: Arnold Leiboff, Old Field, NY (US)

( * ) Notice: Subject to any disclaimer, the term of this patent is extended or adjusted under 35 U.S.C. 154(b) by 933 days.

(21) Appl. No.: 15/505,642

(22) PCT Filed: Sep. 16, 2015

(86) PCT No.: PCT/US2015/050372
§ 371 (c)(1),
(2) Date: Feb. 22, 2017

(87) PCT Pub. No.: WO2016/044388
PCT Pub. Date: Mar. 24, 2016

(65) Prior Publication Data
US 2017/0274126 A1    Sep. 28, 2017

Related U.S. Application Data

(60) Provisional application No. 62/051,262, filed on Sep. 16, 2014.

(51) Int. Cl.
*A61M 5/00* (2006.01)
*H01L 51/52* (2006.01)
(Continued)

(52) U.S. Cl.
CPC .......... *H01L 51/5203* (2013.01); *H01L 29/43* (2013.01); *H01L 51/5293* (2013.01);
(Continued)

(58) Field of Classification Search
CPC ........ A61M 5/00; A61M 25/00; A61M 31/00; A61M 25/16; A61M 39/02; A61M 27/00;
(Continued)

(56) References Cited

U.S. PATENT DOCUMENTS 3,590,820 A    7/1971  Nehra et al.
4,398,910 A    8/1983  Blake et al.
(Continued)

FOREIGN PATENT DOCUMENTS

WO    2016044388 A1    3/2016

OTHER PUBLICATIONS

The Healing Machine: How a Simple Device for Closing Wounds Made Fortunes for its Inventors, for its Marketers, and for Wake Forest University—Until Rivals Claimed it was Too Simple, by Ken Otterbourg, Fortune magazine, Nov. 12, 2012.
(Continued)

*Primary Examiner* — Tatyana Zalukaeva
*Assistant Examiner* — Ilya Y Treyger
(74) *Attorney, Agent, or Firm* — Brian Roffe

(57) ABSTRACT

Wound drain includes a body of elastomeric material. The body includes a flange having a generally planar form and an elongate shaft having a first portion extending to one side of the flange, and optionally a second portion extending to the opposite side of the flange. The flange has a cross-sectional length in a direction perpendicular to a longitudinal direction of the shaft that is larger than a cross-sectional length of the shaft. The shaft includes one or more channels each extending along its entire length or a portion of its length, and along both the first and second portions of the shaft when the second portion of the shaft is present. The shaft also includes one or more longitudinally extending openings that each lead to one of the channels.

21 Claims, 11 Drawing Sheets

(51) Int. Cl.
| | |
|---|---|
| H01L 29/43 | (2006.01) |
| A61M 25/00 | (2006.01) |
| A61M 31/00 | (2006.01) |
| A61M 25/16 | (2006.01) |
| A61M 39/02 | (2006.01) |
| A61M 27/00 | (2006.01) |
| A61F 13/00 | (2006.01) |
| H01L 27/32 | (2006.01) |
| H01L 51/56 | (2006.01) |

(52) U.S. Cl.
CPC ......... *A61F 13/00068* (2013.01); *H01L 27/32* (2013.01); *H01L 51/5262* (2013.01); *H01L 51/56* (2013.01)

(58) Field of Classification Search
CPC ... A61K 9/02; H01L 51/5203; H01L 51/5293; H01L 51/5262; A61F 13/00068
See application file for complete search history.

(56) References Cited

U.S. PATENT DOCUMENTS

| | | | |
|---|---|---|---|
| 4,654,032 | A | 3/1987 | Morales-George |
| 5,100,395 | A | 3/1992 | Rosenberg |
| 8,030,534 | B2 | 10/2011 | Radl et al. |
| 8,067,662 | B2 | 11/2011 | Aali et al. |
| 8,162,907 | B2 | 4/2012 | Heagle |
| 8,215,929 | B2 | 7/2012 | Shen et al. |
| 8,252,971 | B2 | 8/2012 | Aali et al. |
| 8,309,787 | B2 | 11/2012 | Radl et al. |
| 8,334,423 | B2 | 12/2012 | Aali et al. |
| 8,454,567 | B2 | 6/2013 | Long et al. |
| 8,517,918 | B2 * | 8/2013 | Smith ............... A61B 17/3417 600/114 |
| 2003/0050594 | A1 | 3/2003 | Zamierowski |
| 2005/0004536 | A1 | 1/2005 | Opie et al. |
| 2005/0261642 | A1 | 11/2005 | Weston |
| 2006/0079852 | A1 | 4/2006 | Bubb et al. |
| 2007/0282310 | A1 | 12/2007 | Bengtson et al. |
| 2008/0228222 | A1 | 9/2008 | Zamierowski |
| 2010/0016816 | A1 | 1/2010 | Schuessler et al. |
| 2012/0116334 | A1 | 5/2012 | Albert et al. |
| 2014/0257210 | A1 | 9/2014 | Leiboff |

OTHER PUBLICATIONS

Ethicon Product Catalog, Drains-Blake Drains, printed Feb. 14, 2014.
KCI, Products, T.R.A.C. Pad, printed Feb. 14, 2014.
Does Negative Pressure Wound Therapy Have a Role in Preventing Poststemotomy Wound Complications?, Broadus Zane Atkins, MD, Mary Kay Wooten, MSN, Jean Kistler, NP, Kista Hurley, PA-C, G. Chad Hughes, MD, and Walter G. Wolfe, MD, Surgical Innovation, vol. 16, No. 2, Jun. 2009, pp. 140-146.
A Simple Postoperative Umbilical Negative-Pressure Dressing, Federico G. Seifarth, MD, and Colin G. Knight, MD, Advances in Skin & Wound Care, vol. 26 No. 1, Jan. 2013, pp. 26-29.
Incisional Negative Pressure Wound Therapy Significantly Reduces Surgical Site Infection in Open Colorectal Surgery, Allison M. Bonds, M.D., Tessa K. Novick, B.A., L.M.S.W., Jessica B. Dietert, B.S., Farshid Y. Araghizadeh, M.D., Craig H. Olson, M.D., Diseases Colon and Rectum, 2013; vol. 56: pp. 1403-1408.
Negative-Pressure Therapy in the Postoperative Treatment of Incisional Hernioplasty Wounds: A Pilot Study, Carles Olona, PhD; Enric Duque, MD; Aleidis Caro, PhD; Andrea Jime'nez, MD; Felix Moreno, MD; Jose M. Coronas, MD and Vicente Vicente, PhD, Advances in Skin & Wound Care, vol. 27, No. 2, Feb. 2014, pp. 77-80.
A Simple Vacuum Dressing Reduces the Wound Infection Rate of Single-Incision Pediatric Endosurgical Appendectomy, Oliver J. Muensterer, MD, PhD, Richard Keijzer, MD, PhD, Journal of the Society of Laparoendoscopic Surgeons, vol. 15, 2011, pp. 147-150.
Use of vacuum-assisted closure in open incisional hernia repair: a novel approach to prevent seroma formation, M. López-Cano—M Armengol-Carrasco, Hernia (2013) vol. 17, pp. 129-131 (published online Jun. 12, 2011).
Well-wound therapy: use of NPWT to prevent laparotomy breakdown, M. Dutton and K. Curtis,Journal of Wound Care, vol. 21 , No. 8 , Aug. 2012, pp. 386-388.
Incisional Negative-Pressure Wound Therapy Versus Conventional Dressings Following Abdominal Wall Reconstruction A Comparative Study, Alexandra Conde-Green, MD, FICS, Thomas L. Chung, MD, Luther H. Holton, III, MD, Helen G. Hui-Chou, MD, Yue Zhu, MD, MS, Howard Wang, MD, Hamid Zahiri, DO, and Devinder P. Singh, MD, Annals of Plastic Surgery & vol. 71, No. 4, Oct. 2013, pp. 394-397.
Prevention of surgical site infections in high-risk patients with laparotomy incisions using negative-pressure therapy, Aaron U. Blackham, M.D., Jason P. Farrah, M.D., Thomas P. McCoy, M.S., Benjamin S. Schmidt, M.D., Perry Shen, M.D., The American Journal of Surgery (2013) vol. 205, pp. 647-654.
Massive Flap Donor Sites and the Role of Negative Pressure Wound Therapy, Gregg W. Schmedes, Caroline A. Banks, Barry T. Malin, Pamela B. Srinivas and Judith M. Skoner, Otolaryngology—Head and Neck Surgery 2012 147: originally published online Sep. 4, 2012, pp. 1049-1053.
Incisional Negative Pressure Wound Therapy After High-Risk Lower Extremity Fractures, James P. Stannard, MD, David A. Volgas, MD, Gerald McGwin III, PhD, Rena L. Stewart, MD, William Obremskey, MD, Thomas Moore, MD, and Jeffrey O. Anglen, MD, J Orthop Trauma, vol. 26, No. 1, Jan. 2012, pp. 37-42.
Use of negative pressure wound therapy over clean, closed surgical incisions, James P. Stannard, Allen Gabriel, Burkhard Lehner, Int Wound J 2012; 9 (Suppl. 1): pp. 32-39.
Negative Pressure Wound Therapy to Treat Hematomas and Surgical Incisions Following High-Energy Trauma, James P. Stannard, MD, James T. Robinson, BS, E. Ratcliffe Anderson, MD, Gerald McGwin, Jr, PhD, David A. Volgas, MD, and Jorge E. Alonso, MD, The Journal of Trauma:Injury, Infection, and Critical Care, 2006, vol. 60, No. 6, pp. 1301-1306.
Negative Pressure Wound Therapy Is Associated With Resolution of Incisional Drainage in Most Wounds After Hip Arthroplasty, Erik Hansen MD, Joel B. Durinka MD, James A. Costanzo MD, Matthew S. Austin MD, Gregory K. Deirmengian MD, Clin Orthop Relat Res (2013) 471: pp. 3230-3236, Published online: Mar. 29, 2013.
Incisional Vacuum-Assisted Closure Therapy, Andreas H. Gomoll, MD, Albert Lin, MD, and Mitchel B. Harris, MD, J Orthop Trauma, vol. 20, No. 10, Nov./Dec. 2006, pp. 705-709.
Negative pressure wound therapy for skin grafts and surgical wounds healing by primary intention (Review), Webster J, Scuffham P, Sherriff KL, Stankiewicz M, Chaboyer WP, The Cochrane Collaboration. Published by John Wiley & Sons, Ltd., 2013.
Negative pressure wound therapy for management of the surgical incision in orthopaedic surgery, S. Karlakki, M. Brem, S. Giannini, V. Khanduja, J. Stannard, R. Martin, Bone Joint Res 2013; vol. 2, No. 12: pp. 276-284.
Does the Application of Incisional Negative Pressure Therapy to High-RiskWounds Prevent Surgical Site Complications? A Systematic Review, Michael J. Ingargiola, BS, Lily N. Daniali, MD, and Edward S. Lee, MD, eplasty.com. Published Sep. 20, 2013.
First experience with a new negative pressure incision management system on surgical incisions after cardiac surgery in high risk patients, Andrea Colli, Journal of Cardiothoracic Surgery 2011, 6:160.
The Vacuum Assisted Closure Device; A Method of Securing Skin Grafts and Improving Graft Survival, Lynette A Scherer, MD, Stephen Shiver, MD, Michael Chang, MD, J. Wayne M<eredith, MD, John T. Owings, MD, Arch Surg. vol. 137, Aug. 2002, pp. 930-934.
International Search Report for PCT/US2015/050372.
Written Opinion for PCT/US2015/050372.

(56) References Cited

OTHER PUBLICATIONS

Non-crosslinked porcine-derived acellular dermal matrix for the management of complex ventral abdominal wall hernias: a report of 45 cases, by O. Guerra and M. M. Maclin, published online Aug. 10, 2013.
The 'French Fry' VAC technique: hybridisation of traditional open wound NPWT with closed incision NPWT, Karan Chopra, Kashyap K Tadisina and Devinder P Singh, International Wound Journal, Int Wound J 2014; doi: 10.1111/iwj.12266.

\* cited by examiner

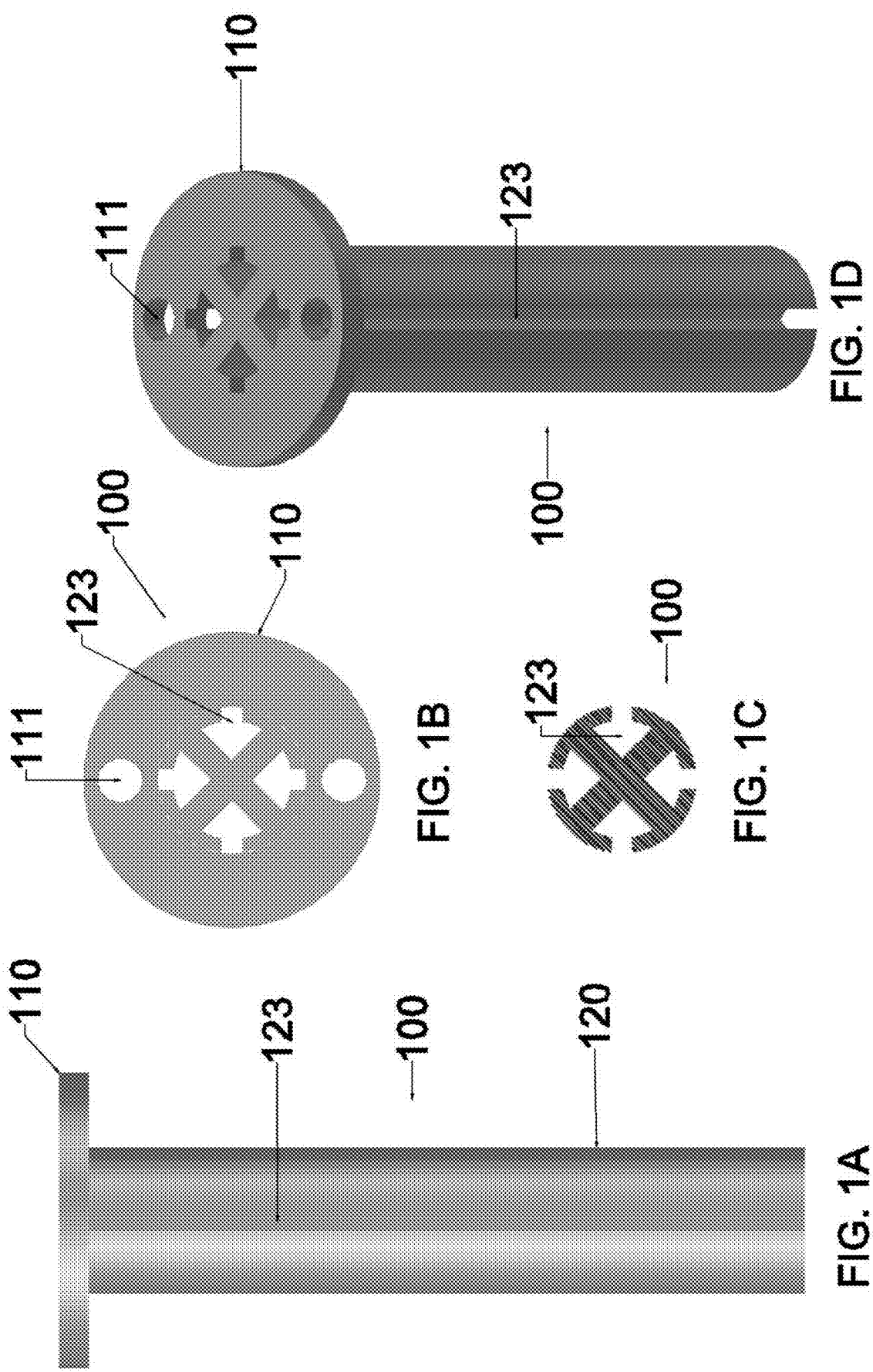

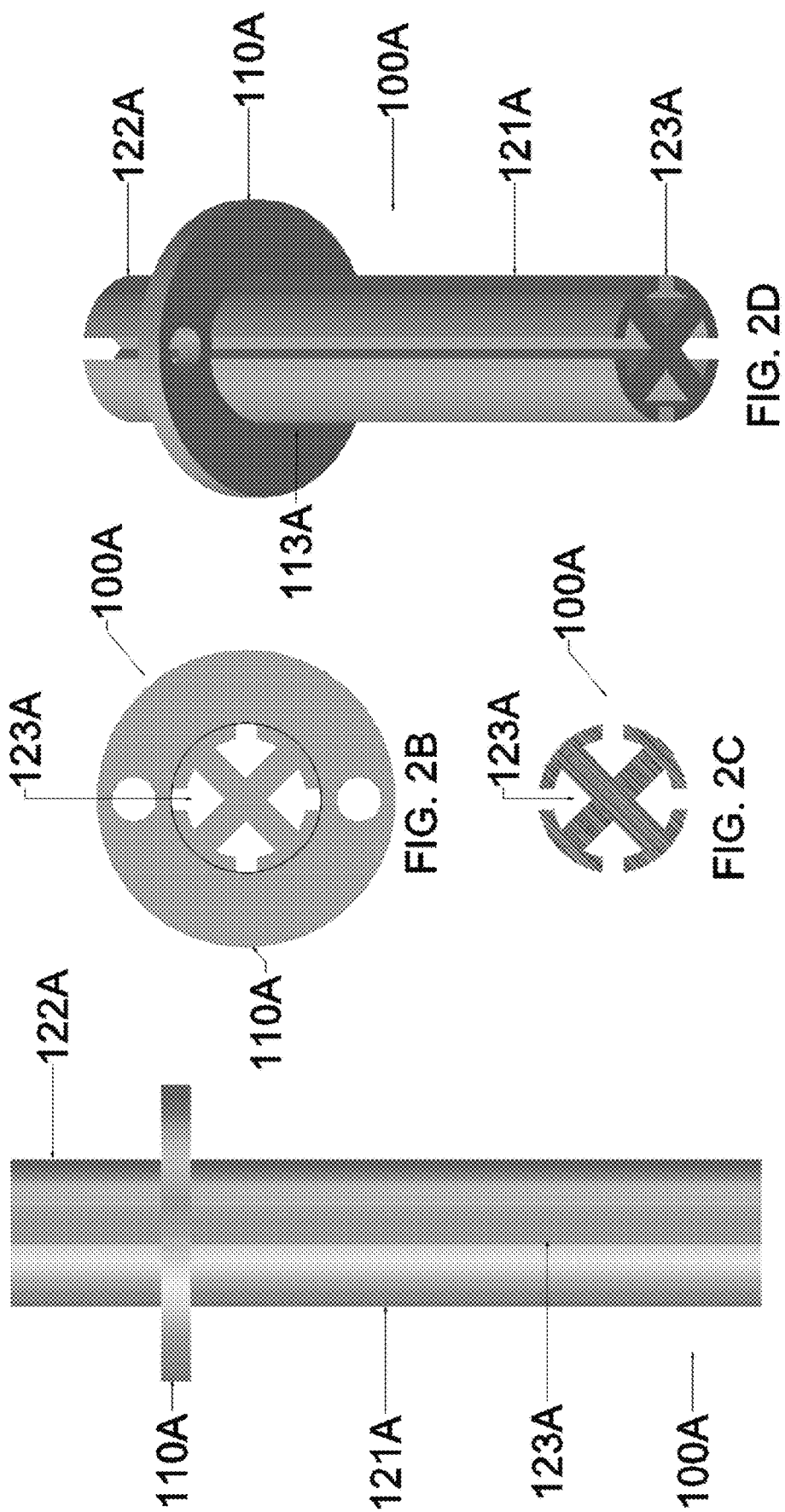

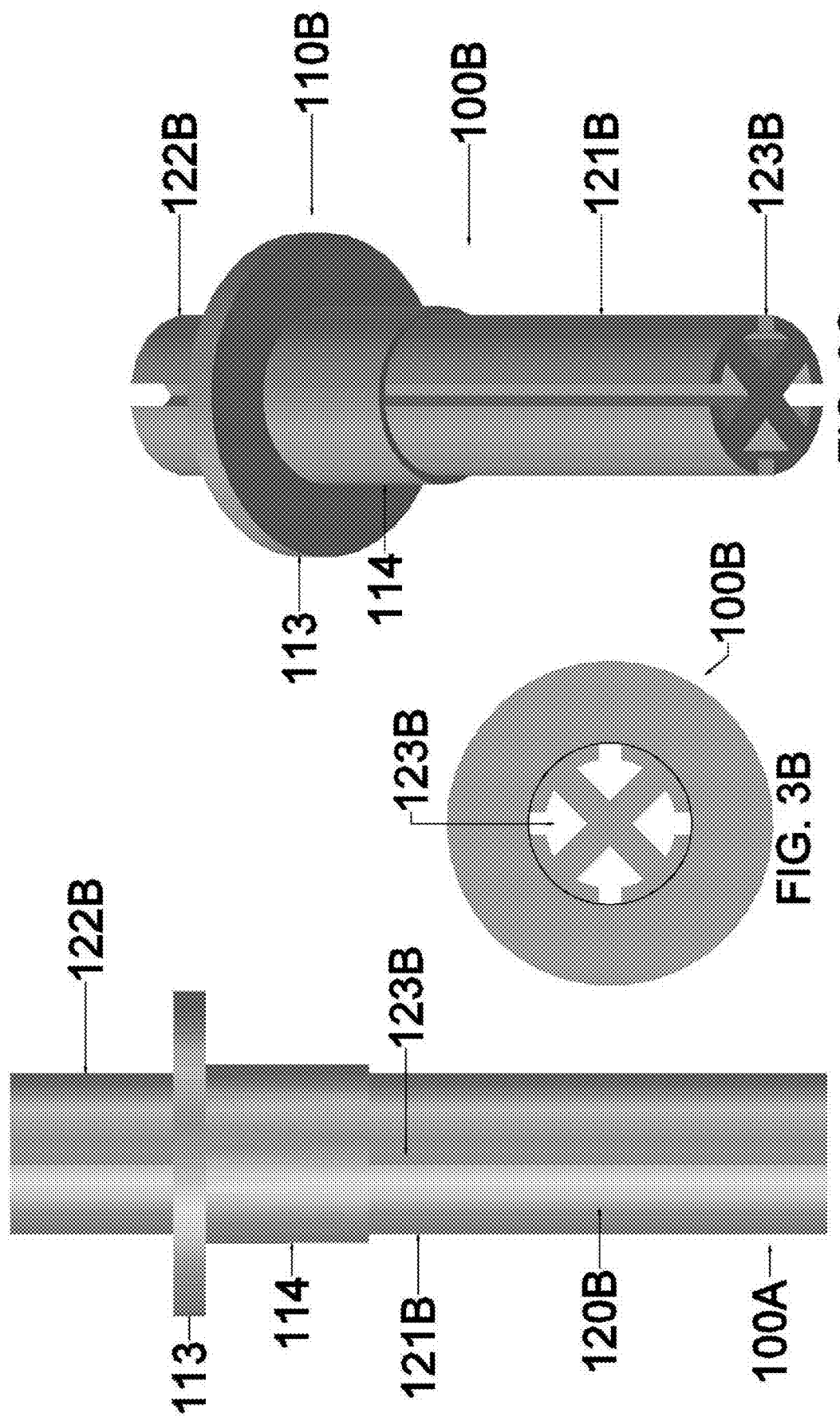

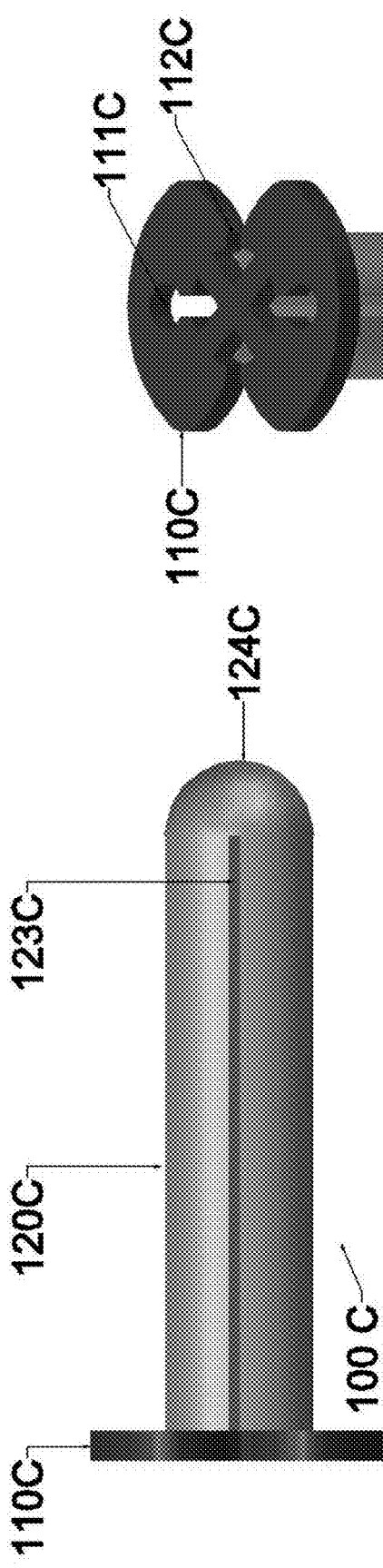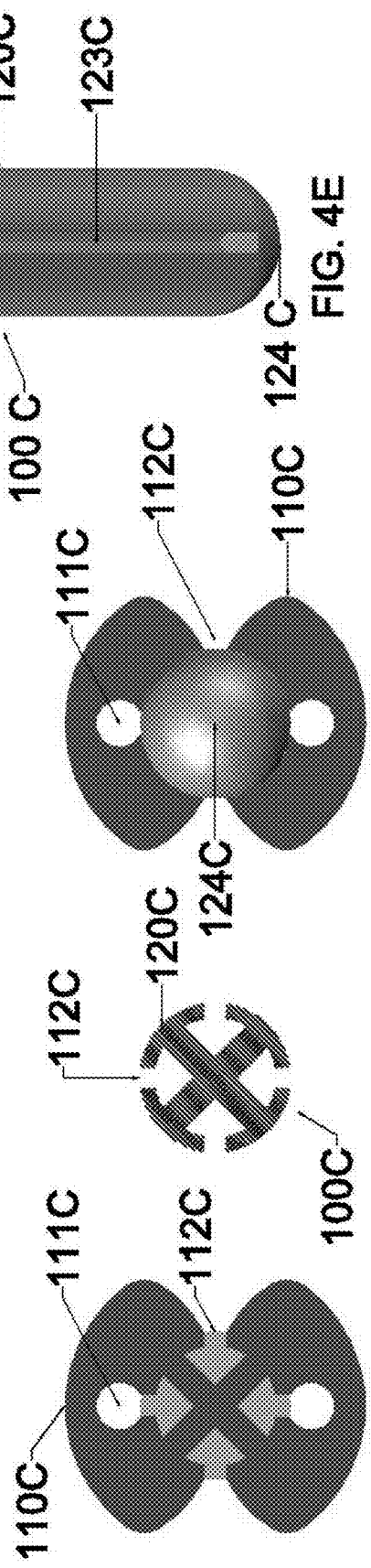

WOUND MANAGEMENT METHOD AND APPARATUS

TECHNICAL FIELD

The present invention relates generally to surgical drains and wound management apparatus and methods for managing a surgical wound after an operation in order to expedite wound healing and reduce the risk of wound complications.

BACKGROUND OF INVENTION

Wound complications, including hematoma, seroma and infection, remain a major problem in surgery. Measures to reduce the rate of wound infection, and complications such as wound dehiscence, evisceration and hernia that may result from wound infection, include the use of antiseptics, antibiotics, film and physical barriers and the placement of wound packing and drains. Alternatively, the skin and subcutaneous fat incision of a wound may be left open or partially open. This is frequently done when it is believed that the wound was substantially contaminated by microbes during the surgical procedure. Although the latter measure may be effective in reducing wound infection rates, postoperative wound care is cumbersome and convalescence prolonged, requiring more intensive treatment at a higher cost.

Although there is evidence that wound drains reduce the rate of wound infection, present methods and apparatus for draining wounds are only partially effective, and the rate of wound infections with these methods and apparatus remains substantial.

Negative pressure wound therapy on open wounds promotes perfusion, reduces swelling, reduces granulation tissue formation by facilitating cell migration and cell proliferation, draws wound edges together and removes exudate and infectious materials. New systems to apply negative pressure wound therapy to closed surgical wounds have been developed and have been shown to reduce rates of wound infection. These systems comprise suction pumps and dressings that provide negative pressure to the surface of a wound, but provide no means to deliver negative pressure directly to the interior of a wound after the skin seals. Reported rates of wound infection when these systems are used are still substantial.

A method of managing a closed surgical wound that provides effective drainage and results in a lower rate of wound complications would be highly advantageous, reducing surgical morbidity and the cost of surgical care.

Bubb et al. (US 20060079852) describes a wound management arrangement and has been considered to disclose a drain adapted to be placed into a closed incisional wound in a position in which it traverses skin through a skin incision 906, and a sponge placed over the wound (FIG. 42). The drain is in flow communication with the sponge. Negative pressure is applied to the wound directly via the sponge overlying the closed incision and thus indirectly to the drain.

Weston et al. (US 20050261642) describes wound treatment appliances and has been considered to disclose a hub secured over an aperture in an adhesive film drape (a tubing member is held in place in the opening 128 by adhesive, FIG. 2A) over the sponge using an adhesive film drape, i.e., supplemental sealing means 176 comprised of an adhesive tape.

Bengston et al. (US 20070282310) is in the field of methods to convey fluid from a wound and has been considered to describe a container interposed between the sponge and vacuum source to collect wound drainage, i.e., inline reservoir 30 to collect withdrawn fluid for disposal, FIG. 4.

Wu et al. (US 20120016321) is in the field of methods for treating an incision and has been considered to disclose configuring a drain as an elastomeric channel drain, i.e., collection chamber comprises a tubular structure; tubing may comprise moldable plastic, moldable materials include elastomeric materials, paragraph 0044, elongate central channel 606, FIG. 6B, wherein at least a portion of the cross-sectional circumference is open for the entire length of the drain, i.e., elongate central channel 606 has open channel configuration that is exposed to incision along a portion if not all of its longitudinal length, paragraph 0069, FIG. 6B.

Dolliver et al. (US 20050192548) is in the field of wound drainage systems and has been considered to disclose configuring a drain as an elastomeric tubular drain, i.e., drain catheter 102 includes a tubular body, paragraph 0020 and may be made of silicone elastomer, paragraph 0022, FIG. 1.

Rosenberg (U.S. Pat. No. 5,100,395) is in the field of fluid drains for wounds and has been considered to disclose securing a drain to skin with at least one stitch that runs through the skin and the drain, i.e., anchoring member 16 includes openings 22 to receive sutures for attaching the anchoring member to skin, col. 3, lines 57-60, FIG. 1).

Schuessler et al. (US 20100016816), in the field healing a surgical wound, has been considered to disclose a longitudinal groove arranged along its undersurface, i.e., underside 212a of divider 212 configured to assist in fluid collection, with divider 212 including longitudinal grooves 214 extending the length thereof, FIG. 8. A drain end is situated in the groove, i.e., channel 216 fluidly communicates each groove 214 with fluid inlet port 213a and vacuum port 213b, FIGS. 8-10.

Zamierowski (US 20080228222) is in the field of medical closure screen devices and has been considered to disclose a clamp that reversibly occludes a tube of a tube assembly, i.e., vacuum source 51 which can be connected to a tube end 38a/40a and to a fluid receptacle 66, and wherein a clamp 62 closes the tube end 38a/40a, FIGS. 4e, 4f).

Zamierowski (US 20030050594) is in the field of wound therapy and has been considered to teach a sponge having a widened end to accommodate a hub, i.e., FIG. 5 shows a sponge 114 sized wider than a hydrophilic sponge 122 to fit connector 110, and wherein a transfer assembly 108 includes elbow connector 110 on top of second sponge drape 112 covering second sponge 114 with an elbow connector 110 mounting a distal end 116 of suction tube 118 that is connected to vacuum source 10, FIG. 5.

Leiboff (WO2014130658) discloses a method for managing a closed incisional wound 1 that includes at least one elastomeric drain 10 inserted partially into the wound, an open cell foam sponge 30 in flow communication with the drain(s) 10 and wound, and to which negative pressure is applied by a vacuum source 70. The negative pressure is transmitted into the otherwise closed wound in order to improve drainage and expedite wound healing.

DISCLOSURE OF INVENTION

A wound drain in accordance with one or more embodiments of the invention includes a body of soft and flexible elastomeric material. The body includes a flange having a generally planar form and an elongate shaft having a first portion extending axially from one side of the flange (below the flange), and optionally a second portion extending axially from the opposite side of the flange (above the flange).

The flange has a cross-sectional length in a direction perpendicular to a longitudinal direction of the shaft that is larger than a cross-sectional length of the shaft. The shaft includes one or more channels each extending along its entire length or a portion of its length, and along both the first and second portions of the shaft when the second portion of the shaft is present.

A wound management system in accordance with one or more embodiments includes a single or multiple soft and flexible elastomeric drains as described above, that are placed into an otherwise closed incisional wound (i.e., a surgical incision which, after completion of a surgical operation, has been closed by suturing or stapling the skin edges together) in such a manner that the drains penetrate through the skin incision so that the flanges of the drains remain external to the body. Each drain may or may not be secured to the skin with at least one stitch that runs through the skin and flange. A sponge may be placed over the drains and wound, and covered and secured with an occlusive adhesive film drape that is secured to the skin surrounding the sponge and wound. Suction may be applied through a tube in flow continuity with the sponge, drains and wound to transmit negative pressure through the wound and to aspirate fluid from the wound into a collection container.

BRIEF DESCRIPTION OF DRAWINGS

The invention, together with further objects and advantages thereof, may best be understood by reference to the following description taken in conjunction with the accompanying drawings wherein like reference numerals identify like elements.

FIG. 1A is a side view of a first embodiment of a drain for use in a method for managing a surgical wound in accordance with this invention.

FIG. 1B is a top end view of the first embodiment of a drain for use in a method for managing a surgical wound in accordance with this invention.

FIG. 1C is a cross-sectional view through the shaft of the first embodiment of a drain for use in a method for managing a surgical wound in accordance with this invention.

FIG. 1D is a perspective view of the first embodiment of a drain for use in a method for managing a surgical wound in accordance with this invention.

FIG. 2A is a side view of a second embodiment of a drain for use in a method for managing a surgical wound in accordance with this invention.

FIG. 2B is a top end view of the second embodiment of a drain for use in a method for managing a surgical wound in accordance with this invention.

FIG. 2C is a cross-sectional view through the shaft of the second embodiment of a drain for use in a method for managing a surgical wound in accordance with this invention.

FIG. 2D is a perspective view of the second embodiment of a drain for use in a method for managing a surgical wound in accordance with this invention.

FIG. 3A is a side view of a third embodiment of a drain for use in a method for managing a surgical wound in accordance with this invention FIG. 3B is a top end view of the third embodiment of a drain for use in a method for managing a surgical wound in accordance with this invention.

FIG. 3C is a perspective view of the third embodiment of a drain for use in a method for managing a surgical wound in accordance with this invention.

FIG. 4A is a side view of a fourth embodiment of a drain for use in a method for managing a surgical wound in accordance with this invention.

FIG. 4B is a top end view of the fourth embodiment of a drain for use in a method for managing a surgical wound in accordance with this invention.

FIG. 4C is a cross-sectional view through the shaft of the fourth embodiment of a surgical drain in accordance with the invention.

FIG. 4D is a bottom end view of the fourth embodiment of a surgical drain in accordance with the invention.

FIG. 4E is a perspective view of the fourth embodiment of a drain for use in a method for managing a surgical wound in accordance with this invention.

BEST MODE FOR CARRYING OUT INVENTION

Figure 5A:
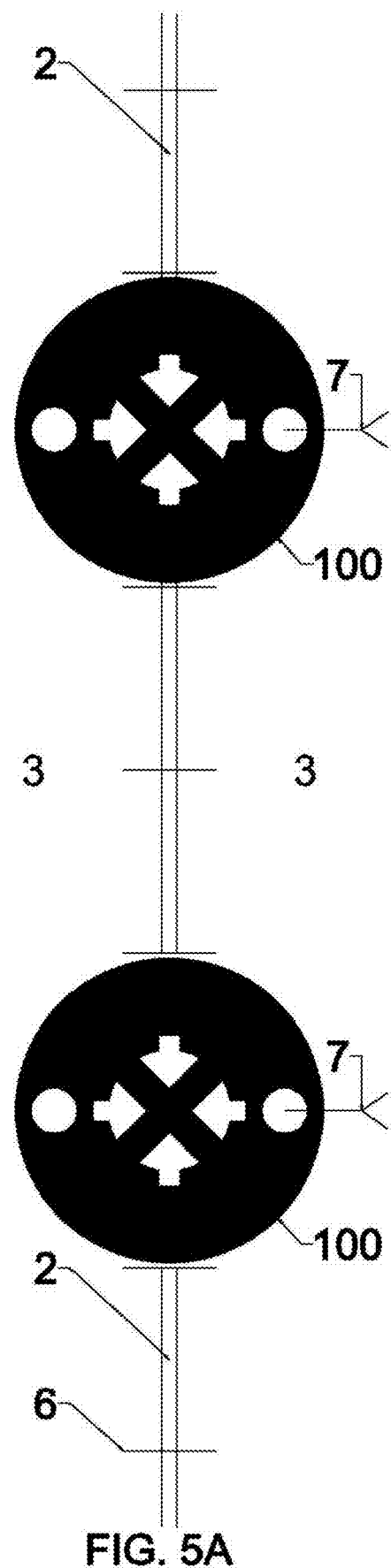
FIG. 5A is an overhead view showing the positions of two of the first embodiment of a drain used in a method for managing a surgical wound in accordance with this invention.
Figure 5B:
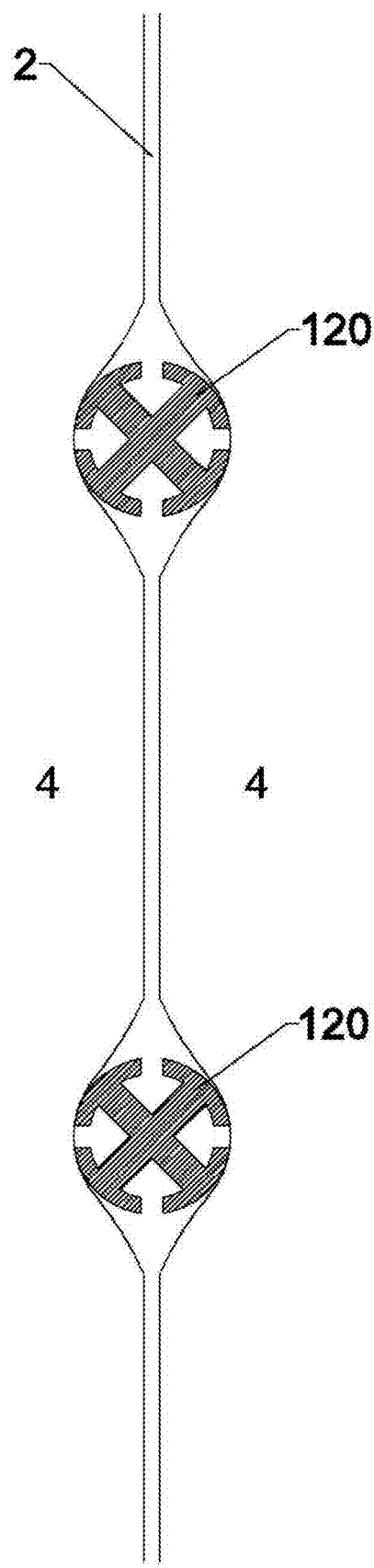
FIG. 5B is a sectional view through the subcutaneous plane of the wound showing cross-sections of the shafts of two of the first embodiment of a drain used in a method for managing a surgical wound in accordance with this invention.

Referring now to FIGS. 1A, 1B, 1C and 1D, a first embodiment of a surgical drain according to the invention is designated generally as 100 and has a body of soft and flexible elastomeric material. The body of the drain 100 includes an elongate shaft 120 extending to one side of a flange 110 that preferably has a generally planar form. The flange 110 may be integral with the shaft 120 or may be fabricated separately and secured to the shaft 120, for example by means of adhesive. The flange 110 may have planar upper and lower surfaces and as illustrated, the shaft 120 extends axially from a side of the lower surface, i.e., has a first portion extending to one side of the flange 110.

The flange 110 has a cross-sectional length, i.e., the length from one edge to an opposite edge and in a direction perpendicular to the axial or longitudinal direction of the shaft 120, that is larger than the cross-sectional length of the shaft 120 to thereby form an overhang. As shown in FIGS. 1B and 1D, the flange 110 has a substantially uniform cross-sectional length and the shaft 120 also has a substantially uniform cross-sectional length. However, the cross-sectional length of the flange 110 and shaft 120 do not have to be uniform. One purpose of the flange 110 in general, and specifically the larger cross-sectional length of the flange 110 relative to the shaft 120, is to limit insertion of the drain 100 into a wound during use using a structure integral to the body of the drain 100. Therefore, the shaft 120 does not have an outer periphery that is contiguous with the outer periphery of the flange 110, but rather attaches to the underside of the flange 110 inward of the outer periphery of the flange 110 to provide the desire overhand of the flange 110. There are other means to achieve this insertion limiting function without requiring substantially uniform cross-sectional lengths for the flange 110 and shaft 120, e.g., providing the cross-sectional length of the flange 110 along only a portion thereof to be greater than the cross-sectional length of the shaft 120 so that the cross-sectional length of the flange 110 is not uniform (see FIGS. 4B and 4E). These means will generally be referred to as integral insertion limiting means.

Flange 110 may contain any number of openings or apertures 111 (see FIGS. 1B and 1D). The flange 110 serves to prevent the drain 100 from receding into the wound during use. It may eliminate the need to suture the drain 100 to the skin. It also provides a convenient means for suturing the drain 100 to the skin, the suture placeable through the flange, either through the soft elastomeric material of the flange or through apertures 111. Shaft 120 contains one or more longitudinal channels 123, providing shaft 120 with a fluted construction. The particular cross-sectional shapes of the flange 110 and shaft 120 shown in FIGS. 1B and 1C are not meant to limit the flange 110 and shaft 120 to any particular cross-sectional shape.

Shaft 120 may be flexible, i.e., made of a flexible, biocompatible material. The material forming the drain 100 may be doped with radiopaque material, or a radiopaque material may be molded into the drain 100, e.g., as a stripe or strand, so that the drain 100 may be detected by radiographic means. Shaft 120 of drain 100 has a preferred diameter of about 5 mm and a preferred length of about 5 cm. Flange 110 has a preferred diameter of about 10 mm and a preferred thickness of about 1 mm. Also, shaft 120 includes one or more channels 123 that extend in the longitudinal direction of the shaft 120, each from a respective opening in the flange 110 to the bottom of the shaft 120. The openings in the flange 110 may have the same cross-sectional shape as the channels 123. The channels 123 may vary in their longitudinal length, although preferably, they extend to the bottom of the shaft 120 and open at the bottom (see FIG. 1D). Thus, a channel 123 may extend along only a portion of the length of the shaft 120.

Shaft 120 has a generally cylindrical form with the outer circumferential surface of the shaft 120 being interrupted by the openings of the channels 123 (see FIG. 1D). Channels 123 should be positioned to enable the shaft 120 to maintain its general form after insertion through a wound incision into the skin (discussed below). It is important that the channels 123 be open after the shaft 120 is inserted, both in the longitudinal direction internal of the shaft 120 and the openings in the circumferential surface of the shaft 120, because the drainage provided by the drain 100 occurs through the channels 123 and drainage fluid enters into the channels 123 through the openings in the circumferential surface (as well as through the opening at the longitudinal end of the channel 123).

Referring now to FIGS. 2A, 2B, 2C and 2D, a second embodiment of a surgical drain according to the invention is designated generally as 100A and its body includes a fluted shaft 120A, having longitudinal channels 123A, extending through and to both sides of flange 110A, so that a portion 121A of shaft 120A is situated below flange 110A, and a portion 122A of the shaft 120A is above the flange 110A. The flange 110A may be integral with the shaft or may be fabricated separately and secured to the shaft, for example by means of adhesive. Other features of drain 100A may be the same as those of drain 100 described above with reference to FIGS. 1A-1D.

Referring now to FIGS. 3A, 3B and 3C, a third embodiment of a drain in accordance with the invention is designated generally as 100B, and its body has a flange 110B fabricated separately and secured to a shaft 120B. The flange 110B may be a planar disc, a cylindrical collar, or a T shaped structure, having a head 113 and tubular stem 114, as shown in FIGS. 3A-3C. The stem 114 of the T of the flange 110B may be directed upward toward the shorter side of the shaft 120B, or downward toward the longer side of the shaft 120B. An advantage of the latter configuration is that when placed into the wound with the short end external to the skin, as intended, the flange stem shields the epithelial layer of skin from being in direct contact with channels of the drain 100B, sponge and negative pressure applied through the sponge, and thereby prevents damage to this sensitive layer.

FIGS. 4A, 4B, 4C, 4D and 4E show an embodiment of an elastomeric surgical drain 100C in which the body has a generally planar flange 110C, an elongate shaft 120C and a tip 124C at an end of the shaft 120C. Shaft 120C contains one or more longitudinal channels 123C, each of which is continuous with an aperture 111C or a groove 112C in the flange 110C, i.e., in communication therewith. Shaft 120C may be flexible, i.e., made of a flexible, biocompatible material. The channels 123C provide the shaft 120C with a fluted construction. Preferably, there is a one-to-one correspondence between the channels 123C in the shaft 120C and the apertures 111C or grooves 112C in the flange 110C, i.e., each channel 123C communicates with a single aperture 111C or a single groove 112C. Other flow communication arrangements are possible. In a preferred embodiment, there are two grooves 112C on opposite sides of the flange 110C and thus two corresponding channels 123C in the shaft 120C.

In the plane of flange 110C, apertures 111C are completely surrounded by elastomeric material, whereas grooves 112C are not, i.e., grooves 112C are open radially outward (as shown in FIG. 4B). As such, apertures 111C and grooves 112C may be formed after the flange 110C, i.e., as perforations made into a solid material forming the flange 110C. Further, in the plane of the flange 110C, the dimensions of the apertures 111C preferably exceed the cross-sectional dimensions of the respective communicating channels 123C of the shaft 120C.

The flange 110C has a cross-sectional length, i.e., the length from one edge to an opposite edge and in a direction perpendicular to the longitudinal direction of the shaft 120C, that is larger than the cross-sectional length of the shaft 120C, i.e., one or more portions of the flange 110C extend radially outward beyond the outermost radial edge of the shaft 120C. Some portions of the flange 110C may have a cross-sectional length that is the same as or smaller than the cross-sectional length of the shaft 120C, e.g., those portions at which the grooves 112C are formed.

Channels 123C preferably stop short of tip 124C, i.e., extend only along a portion of the longitudinal dimension of the shaft 120C, so that the surface of tip 124C may be smooth without openings. Each channel 123C may end abruptly in a squared-off manner, or become more shallow in the direction toward the tip 124C and disappear as it approaches the tip 124C. The particular cross-section shapes of the apertures 111C, grooves 112C and channels 123C shown in FIGS. 4B-4E, are not meant to limit the invention in any manner whatsoever. Also, the particular cross-sectional shapes of the flange 110C and shaft 120C shown in FIGS. 4A-4E are not meant to limit the flange 110C and shaft 120C to any particular cross-sectional shape.

Drains 100, 100A and 100C may be formed as a single unit using a molding process, preferably from a soft and flexible elastomeric material. The drains may thus be a unitary structure, a single piece structure, a homogenous structure, and combinations of such. The particular singular material or combination of materials, such as biocompatible materials, from which the drains are formed would be readily apparent to those skilled in the art of wound drainage in view of the disclosure herein. Also, the molding process used to form the drains may be any process that is capable of providing the drains with the characteristics disclosed herein.

Referring now to FIGS. 5A, 5B, 6A and 7A, an exemplifying, non-limiting method for draining a surgical wound 1 and applying negative pressure to the surgical wound 1 in accordance with the invention includes closing a surgical incision 2 by approximating the skin 3 on either side with staples or sutures 6, typically placed in an interrupted manner. The method may entail trimming the shaft 120 of at least one drain 100 to optimal length, inserting the shaft 120 of at least one drain 100 between staples or sutures 6 through the incision 2 in the skin 3, perpendicular or nearly perpendicular to the plane of the skin 3, into a subcutaneous layer 4 of the wound 1 so that the end of each drain 100 is situated above a closed fascial layer 5 of the wound 1 and the flange 110 is situated above the skin 3.

FIG. 5A shows the use of two drains 100, although the actual number used for each wound draining may vary as determined, e.g., by the surgeon or other operatory personnel. Drains 100 are shown extending perpendicular to the skin 3 and fascia 5, but in use, a portion of the drain may lie in another orientation, for example, parallel to the fascia as the drain traverses under a skin flap or between tissue planes.

Each drain 100 may be secured in this position by a suitable securing mechanism or technique, for example, with a suture tie 7 by passing a suture needle and thread through the skin and the flange 110 of the drain 100 and tying to form one or more stitches that pass through the skin 3 and flange 110 of the drain 100. The suture may be passed through the aperture 111 in the flange 110 or through the elastomeric substance of the flange. Instead of a suture tie 7, other comparable securing mechanisms known to those skilled in this field may be used. Such securing mechanisms are collectively referred to as securing means herein.

To avoid damage to intact skin by suction to be applied through a sponge 30 that will be placed over the drains 100, protective adhesive film strips 20 are placed along both sides of the incision 2 for the length of the incision 2 (see FIGS. 6A and 7A) or a single adhesive film dressing can be placed directly over the incision. If placed directly over the incision, the adhesive film dressing can be applied prior to implantation of the drains, and can be punctured to create openings through which the drains can be implanted, with the shaft 120 passing through the adhesive film strips 20 and skin and the flange 110 remaining above the adhesive film strips 20.

Adhesive film strips 20 and the adhesive film dressing described in the previous paragraph, serve to protect the underlying skin from damage caused by direct contact with a sponge under negative pressure. The semipermeable nature of the adhesive film dressings and strips allows vapor produced by the skin to traverse the film and be absorbed by the sponge.

An open cell foam sponge 30 is then preferably placed over drains 100 to cover the drains, incision 2 (see FIGS. 6A and 7A) and protective adhesive film strips 20 or dressing. The sponge 30 would preferably be long enough so it could cover most surgical incisions and in use would be cut to the length of the surgical incision, if necessary. Dimensions of approximately 1.5 cm thick, 5 cm wide and 30 cm long for the sponge 30 are preferable. The width of the sponge may be narrower with one location on the sponge, e.g., one end 31 of the sponge 30, may be expanded (to for example, 5 cm), and possibly assume a substantially circular shape, in order to better accommodate a suction dome 51 and its flange 52. Although a single sponge 30 is shown, if necessary, multiple sponges may be used.

An occlusive transparent adhesive film drape 40 with its adhesive surface facing downward, is preferably placed over the sponge 30 to cover the entire sponge 30 and incision 2, and then firmly secured to the healthy skin 3 around the wound margin. Coverage of the entire sponge 30 and incision 2 by the adhesive film drape 40 prevents an air leak from developing that would adversely impact the vacuum and suction application. One or more additional adhesive film drapes or dressings may be placed over those described to reinforce all seals.

Figure 6A:
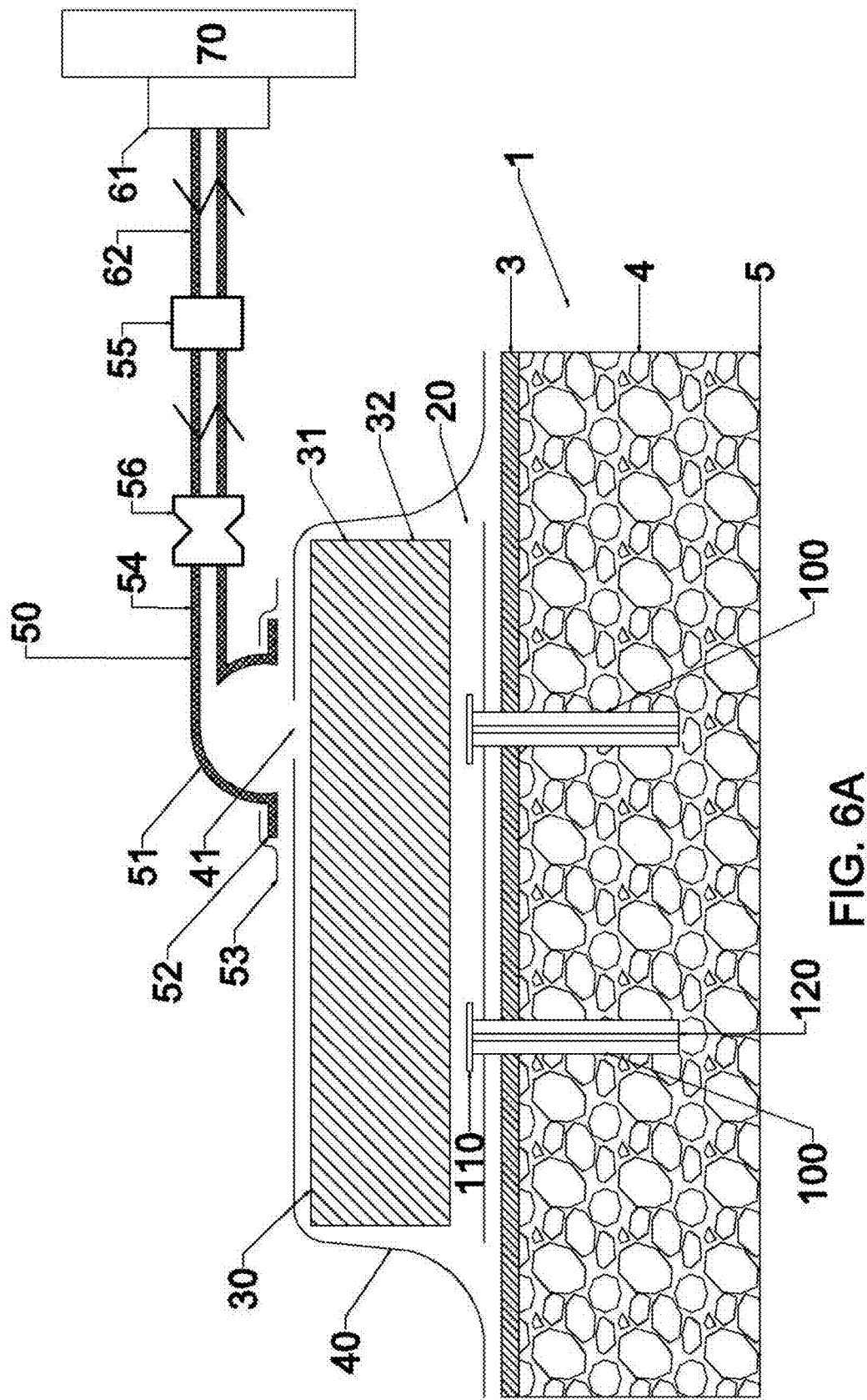
FIG. 6A is a longitudinal sectional view of the use of apparatus in a method for managing a surgical wound in accordance with this invention, showing two of the first embodiment of the drain.
Figure 7A:
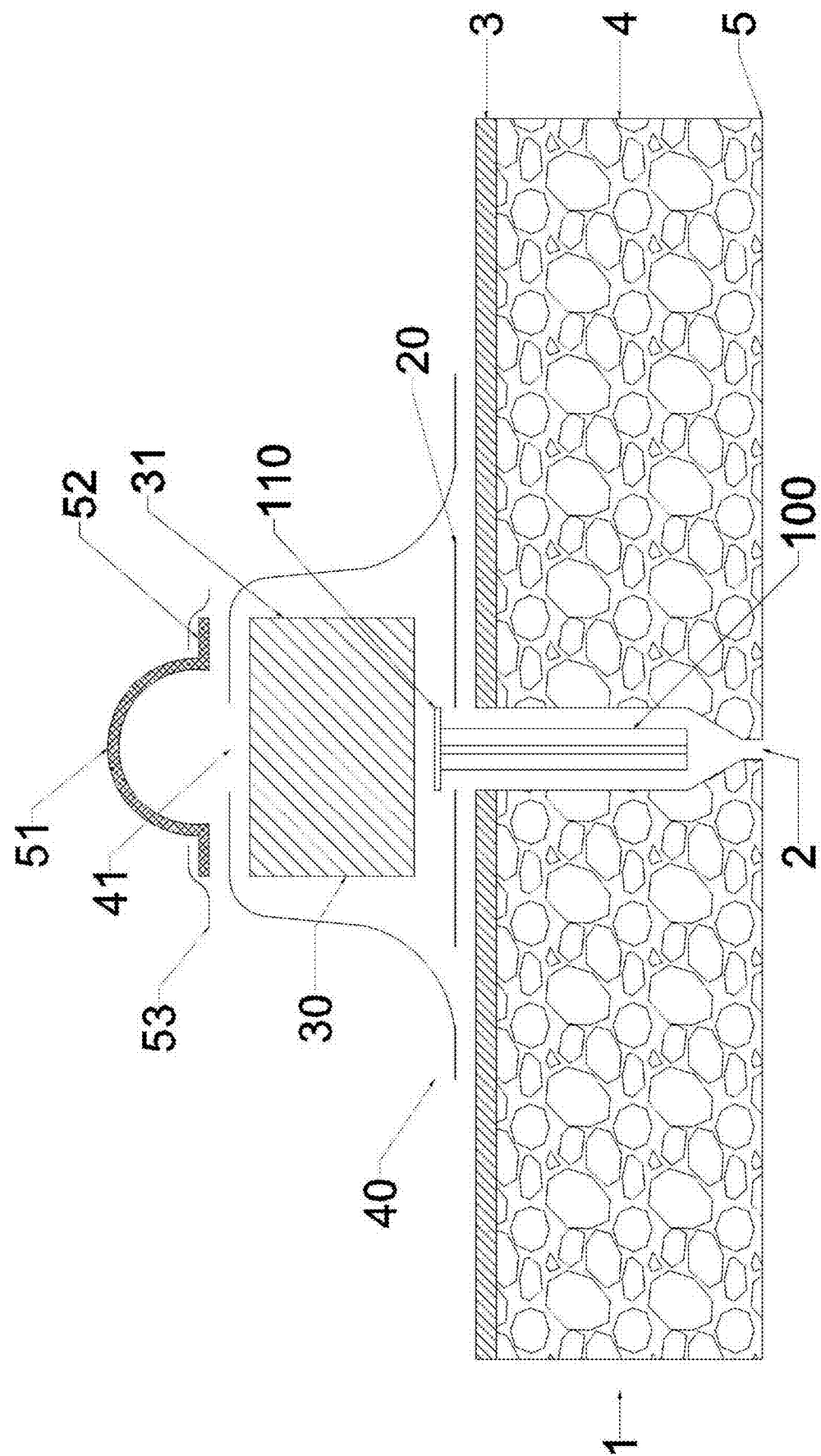
FIG. 7A is a transverse sectional view of the apparatus for use in a method for managing a surgical wound in accordance with this invention, showing the first embodiment of the drain.

An aperture 41 is cut into or otherwise provided in the adhesive film 40 above the sponge 30 (see FIGS. 6A and 7A). Onto this aperture 41, a suction dome 51 or other hub of a tube assembly 50 is secured, for example, by means of an adhesive film collar 53 that may be attached to the flange 52 of suction dome 51. Alternatively, a hub of a different design, e.g., a short tube with side perforations or channels, can be inserted on top of or through a portion of the sponge and an adhesive film dressing used to seal an interface between the hub and sponge 30 or tube 54 and sponge 30 so that no air leak would ensue when negative pressure is applied to the sponge 30 through the tube 54. Suction dome 51 is provided preferably integrally attached to tube 54 of tube assembly 50. A connector 55 is provided at the end of tube 54 opposite suction dome 51, that connects to a tube 62 from container 61, either directly or by means of a compatible connector fitting on the end of tube 62. Tube 54 may have a single lumen as shown or multiple lumens in flow communication with suction dome 51 and connector 55. The lumen of tube 54 is placed in flow communication with a suction source 70. A tubing clamp 56 is provided to occlude the tube lumen when circumstances require that tube 54 be separated from the suction source 70, for example, when the patient ambulates.

When the suction source 70 is activated, constant or variable negative pressure is applied to the sponge 30, each drain 100 and wound 1. Free fluid in the wound 1 is aspirated through channels 123 of each wound drain 100 (see FIGS. 1A-1D), into and through the sponge 30, into the suction dome 51 of tube assembly 50, and through tube 54 and tube 62 into a collection container 61 that is provided with negative pressure by the suction source 70. The adhesive film drape 40 and adhesive film collar 53 impede the ingress of air and allow a partial vacuum to form within the wound 1, reducing its volume and facilitating the removal of fluid. Alternative arrangements to the adhesive film drape 40 and adhesive film collar 53 may be used which function to control air flowing into the sponge 30 at a reduced rate, providing for a constant flow in the sponge 30 and tubing (tube assembly 50, and tubes 54, 62) and still allowing for the maintenance of negative pressure.

Figure 6B:
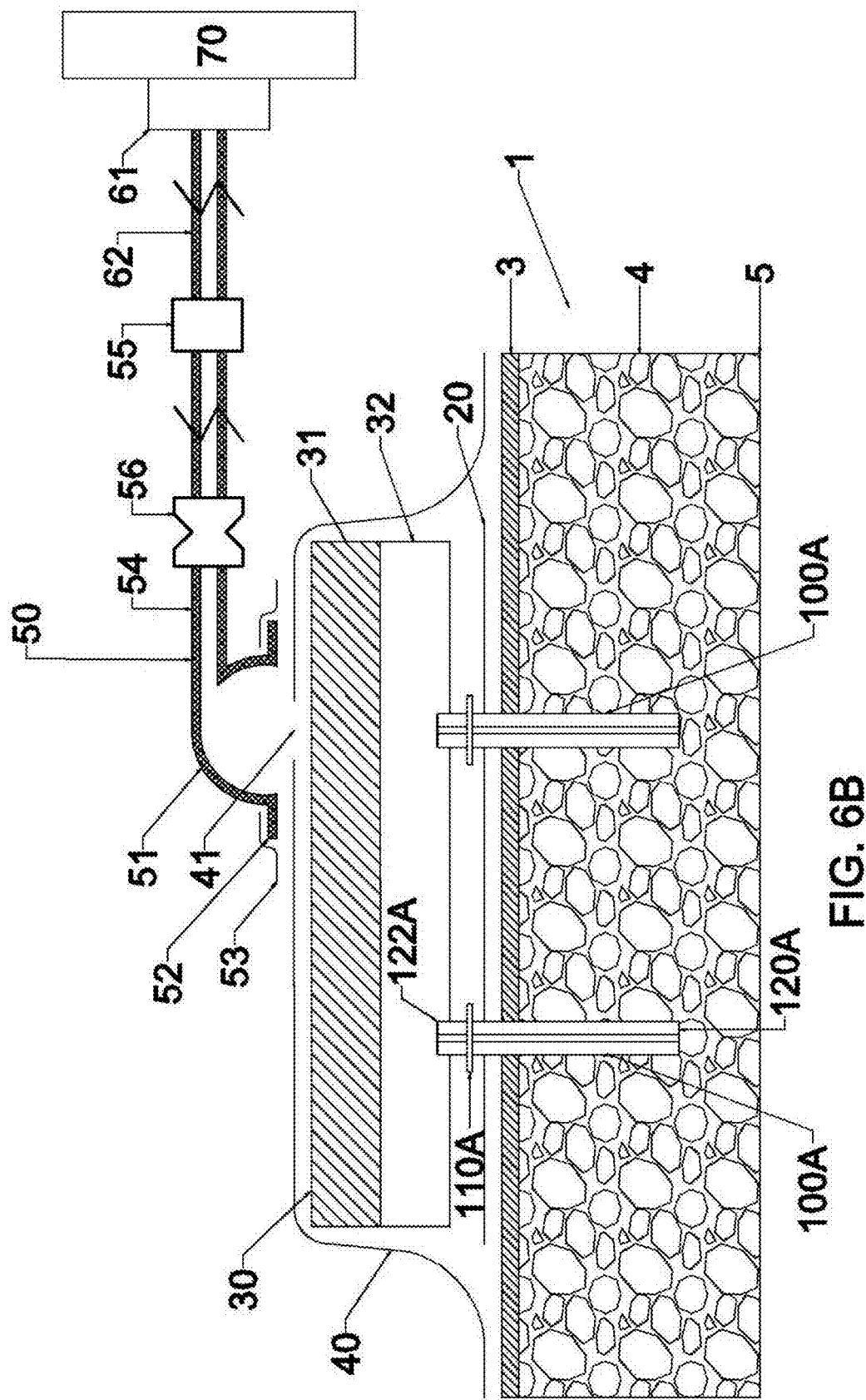
FIG. 6B is a longitudinal sectional view of the use of apparatus in a method for managing a surgical wound in accordance with this invention, using two of the second embodiment of the drain.
Figure 7B:
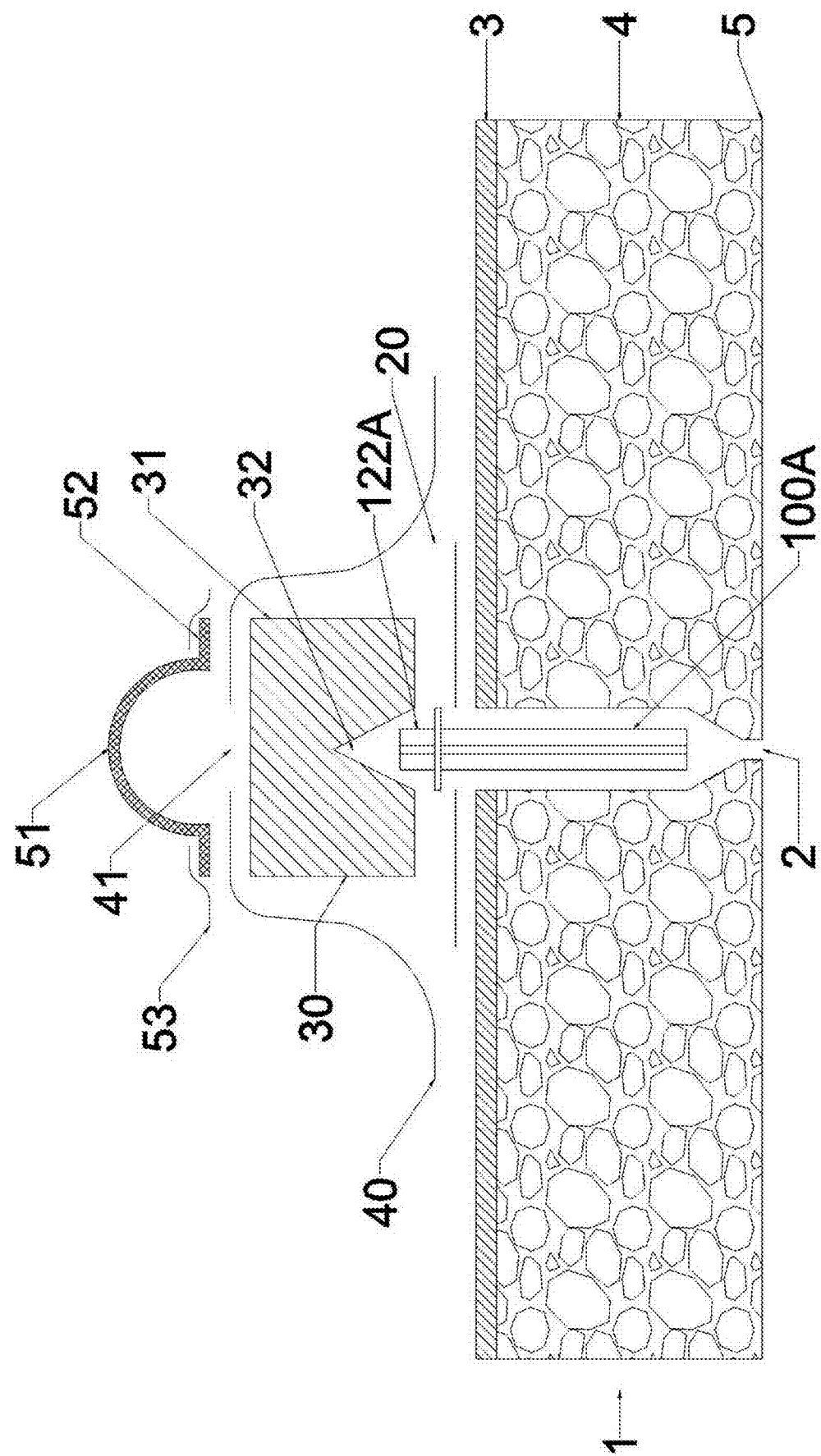
FIG. 7B is a transverse sectional view of the apparatus for use in a method for managing a surgical wound in accordance with this invention, showing the second embodiment of the drain.

Sponge 30 may contain one or more grooves or slits 32 on its undersurface (FIGS. 6B and 7B) into which portions 122A of shaft 120A of drain 100A or 122B of shaft 120B of drain 100B insert. This allows the sponge 30 to be restrained by the drains, so that the sponge 30 stays more readily in place over the incision 2 and drains while an adhesive film drape 40 is applied.

Alternatively, foam sponge 30 may be provided with narrow strips of adhesive film fixed, for example, to its undersurface by adhesive or other technique known in the art. These narrow strips may run the full length of foam sponge 30, or a portion of the length, one strip on either side of the groove, neither strip covering the groove, and be provided with liners, so that when the liners are removed the sponge 30 may be secured in place over the incision and drains, to the skin by the adhesive film strips, with portions 122A of shaft 120A of drain 100A or 122B of shaft 120B of drain 100B projecting into the groove 32.

Drains 100, 100A and 100B may be provided at a longer length, e.g., with shaft 120 or portion 121A of shaft 120A, or portion 121B of shaft 120B, preferably about 5 cm, and can be individually trimmed by the surgeon to a length suitable for its position in the incision. Drains 100D may be provided in varying lengths so as to accommodate varying thicknesses of the fatty subcutaneous layer and wound depths.

Figure 8:
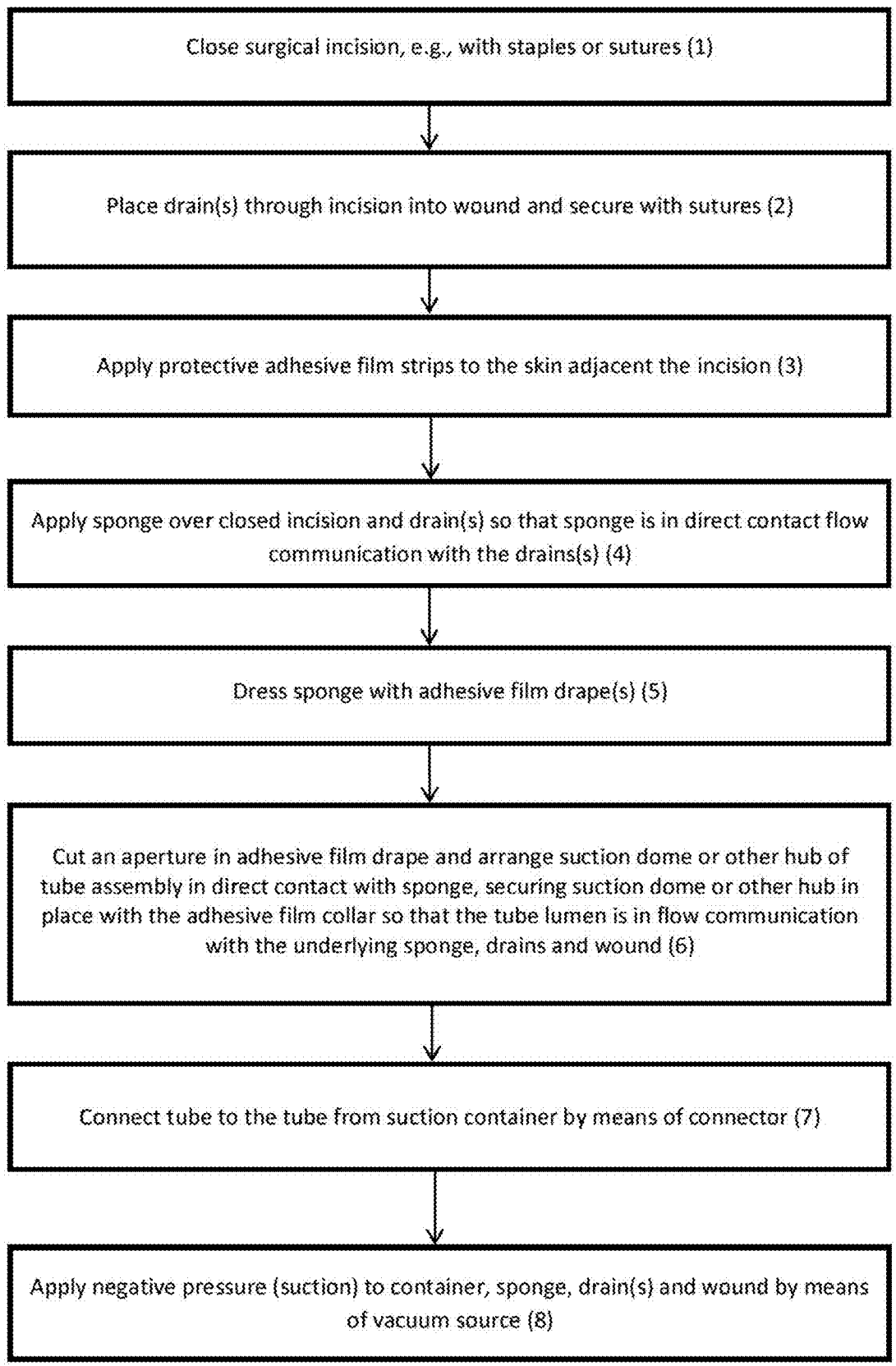
FIG. 8 is a flow chart showing the basic steps of the method of this invention.

To summarize the basic steps of the method of this invention, which can be seen in chart form in FIG. 8:

Step 1—A surgical incision is closed by approximating skin edges with staples or sutures, or other securing means.

Step 2—One or more channel drains having a flange are placed through the incision into the wound space so that the flange is situated above the skin and the end of the shaft above the fascia. Selection of the number and type of drain is at the discretion of the surgeon, whether one or more of drains 100-100D described above or another comparable drain.

Step 3—One or more protective adhesive film strips are applied to the skin adjacent the incision.

Step 4—One or more sponges is applied over the closed incision and drain(s) so that each sponge is in direct contact flow communication with the drain(s).

Step 5—Each sponge is dressed with one or more adhesive film drapes, to cover and maintain the sponge in a substantially air-tight manner against the incision and drain(s).

Step 6—A connector, tube, suction dome or other hub and adhesive film collar assembly is arranged to be in direct contact with the sponge(s), by cutting an aperture in the adhesive film over the sponge(s), and securing a suction dome or other hub in place with the adhesive film collar so that the tube lumen is in flow communication with the underlying sponge(s), drain(s) and wound.

Step 7—The tube is connected to an additional tube from a suction container by means of the connector.

Step 8—Negative pressure is applied to the container, sponge(s), drain(s) and wound by means of a vacuum source.

This order of steps is not an absolute requirement and may be altered. For example, step 3 may be performed before step 2.

While the apparatus and methods of this invention may be used at the time of the surgical operation, the same apparatus and methods may be used in the postoperative period to drain the wound if a wound infection or seroma develops or is suspected.

With the foregoing apparatus and methods, several objectives and advantages are achieved, such as providing apparatus and methods for expediting healing of a surgical wound, providing apparatus and methods for reducing the chance of developing a wound infection, providing apparatus and methods for reducing labor required for postoperative care of a surgical wound, and/or providing apparatus and methods to reduce cost of postoperative care of a surgical wound.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

The invention claimed is:

1. A wound drain, comprising:
   a body of elastomeric material, the body including an elongate shaft and a flange, the flange having a portion extending radially outward from the shaft to define a surface radially outward from an outer surface of the shaft that operatively limits insertion of the shaft into a wound, the shaft having a first portion extending axially from one side of the flange, at least a portion of the flange having a cross-sectional length in a direction perpendicular to a longitudinal direction of the shaft that is larger than a cross-sectional length of the shaft,
   the shaft having a circumferential surface and including a plurality of separated channels each extending in the longitudinal direction of the shaft along a portion of a length of the shaft, and a plurality of longitudinally extending openings in the circumferential surface each leading to a respective one of the plurality of channels, the flange including a plurality of apertures or grooves each in flow communication with a respective one of the at least one channel plurality of channels of the shaft,
   whereby when used, draining fluid from the wound passes through the longitudinally extending openings into the plurality of channels of the shaft and through the plurality of channels of the shaft and outward through the plurality of apertures or grooves in the flange.

2. The wound drain of claim 1, wherein the body has a unitary structure and the flange has a generally planar form.

3. The wound drain of claim 1, wherein the flange has an upper surface and a lower surface on an opposite side of the flange from the upper surface, and the shaft extends only from the lower surface, each of the plurality of apertures or grooves in the flange extending between the upper and lower surfaces, opening into both the upper and lower surfaces of the flange and being surrounded by elastomeric material of the flange, each of the plurality of apertures or grooves in the flange has having a cross-sectional dimension that is equal to or exceeds the cross-sectional dimension of the respective one of the plurality of channels of the shaft.

4. The wound drain of claim 1, wherein the plurality of channels of the shaft consists of four channels, the plurality of openings of the shaft consists of four longitudinally extending openings each leading to a respective one of the four channels of the shaft, and the plurality of apertures or grooves in the flange consists of four apertures or grooves that each are continuous with a respective one of the four channels of the shaft.

5. The wound drain of claim 1, wherein the shaft has a smooth tip, the plurality of channels in the shaft terminating at a location apart from the tip.

6. The wound drain of claim 1, wherein the shaft has a second portion extending axially from an opposite side of the flange from the first portion, the plurality of channels of the shaft extending in both the first and second portions and being continuous through a plane of the flange.

7. The wound drain of claim 1, wherein the flange has a uniform cross-sectional length and the shaft has a uniform cross-sectional length less than the cross-sectional length of the flange, the cross-sectional length of the flange being a largest cross-sectional length of the wound drain.

8. A wound drain, comprising:
a body of elastomeric material, the body including an elongate shaft having a circumferential surface and including a plurality of channels each extending longitudinally along at least a portion of a length of the shaft, a plurality of longitudinally extending openings in the circumferential surface each leading to respective one of the plurality of channels, and integral insertion limiting means that limit insertion of the shaft into an incision, the insertion limiting means including a portion that extends radially outward from the shaft to define a surface radially outward from an outer surface of the shaft that operatively limits insertion of the shaft into the incision,
the insertion limiting means including a plurality of apertures or grooves each in flow communication with a respective one of the plurality of channels of the shaft, whereby when used, draining fluid from a wound passes through the plurality of longitudinally extending openings into the plurality of channels of the shaft and through the plurality of channels of the shaft and outward through the plurality of apertures or grooves.

9. A method for draining a wound and providing negative pressure to a wound, comprising:
inserting into a wound at least one drain including a body of elastomeric material, the body including an elongate shaft and a flange having a portion extending radially outward from the shaft to define a surface radially outward from an outer surface of the shaft that operatively limits insertion of the shaft into a wound, the shaft having a first portion extending axially from one side of the flange, at least a portion of the flange having a cross-sectional length in a direction perpendicular to a longitudinal direction of the shaft that is larger than a cross-sectional length of the shaft, the shaft having a circumferential surface and including a plurality of channels extending in the longitudinal direction of the shaft along a portion of a length of the shaft, and a plurality of longitudinally extending openings in the circumferential surface each leading to a respective one of the plurality of channels, the flange including a plurality of apertures or grooves each in flow communication with a respective one of the plurality of channels of the shaft,
placing at least one sponge over the flange of the at least one drain, and
applying negative pressure from a location over the sponge to urge fluid in the wound to pass through the longitudinally extending openings into the plurality of channels of the shaft and through the plurality of channels of the shaft and through the communicating plurality of apertures or grooves in the flange and into the sponge and through the sponge to be collected in a container.

10. The method of claim 9, further comprising inserting the at least one drain into the wound perpendicular to a plane of a body wall and such that the flange remains above a surface of skin around the wound.

11. The method of claim 9, wherein the wound is a surgical incision and skin around the incision is closed so that only the shaft of the at least one drain perforates the incision.

12. The method of claim 9, wherein the at least one drain comprises a plurality of drains, further comprising placing the drains along a length of the wound.

13. The method of claim 12, wherein the step of placing at least one sponge over the flange of the at least one drain comprises placing at least one sponge over the flanges of the plurality of drains, the method further comprising securing the at least one sponge with an occlusive adhesive membrane that is fixed to the skin surrounding the at least one sponge and wound.

14. The method of claim 13, further comprising attaching a tube to an aperture in the membrane and applying the negative pressure through the tube to the at least one sponge, the plurality of drains and wound.

15. The method of claim 9, wherein the step of placing at least one sponge over the flange of the at least one drain comprises placing a sponge over the flange of the at least one drain, the method further comprising securing the sponge with an occlusive adhesive membrane that is secured to the skin surrounding the sponge and the wound.

16. The method of claim 15, further comprising attaching a tube to an aperture in the membrane and applying the negative pressure through the tube to the sponge, the at least one drain and the wound.

17. The method of claim 16, further comprising attaching an internal space of the tube to the sponge in flow communication with a pump that provides the negative pressure to the sponge and through the at least one drain to the wound.

18. The method of claim 15, wherein the shaft has a second portion extending axially from an opposite side of the flange than the first portion of the shaft and the sponge has a groove to accommodate the second portion of the shaft.

19. The wound drain of claim 1, wherein each of the plurality of longitudinally extending openings extends for the length of the respective one of the plurality of channels such that at every cross-sectional plane along the length of the channel, not including a plane of the flange, there is direct flow communication in that cross-sectional plane between an interior of the channel and space external to the body through the respective one of the plurality of longitudinally extending openings.

20. The method of claim 9, wherein each of the plurality of longitudinally extending openings extends for the length of the respective one of the plurality of channels such that at every cross-sectional plane along the length of the channel, not including a plane of the flange, there is direct flow communication in that cross-sectional plane between an interior of the channel and space external to the body through the respective one of the plurality of longitudinally extending openings.

21. A method for draining a wound, comprising:
inserting into a wound at least one drain including a body of elastomeric material, the body including an elongate shaft and a flange having a portion extending radially outward from the shaft to define a surface radially outward from an outer surface of the shaft that operatively limits insertion of the shaft into the wound, the shaft having a first portion extending axially from one side of the flange, at least a portion of the flange having a cross-sectional length in a direction perpendicular to a longitudinal direction of the shaft that is larger than a cross-sectional length of the shaft, the shaft having a circumferential surface and including a plurality of channels extending in the longitudinal direction of the shaft along a portion of a length of the shaft, and a plurality of longitudinally extending openings in the circumferential surface each leading to a respective one of the plurality of channels, the flange including a plurality of apertures or grooves each in flow communication with a respective one of the plurality of channels of the shaft, whereby when the at least one drain is in place in the wound and negative pressure applied to an area above and proximate to the at least one drain, bodily fluid in the wound passes through the plurality of longitudinally extending openings into the plurality of channels of the shaft and through the plurality of channels of the shaft and through the communicating plurality of apertures or grooves in the flange.

* * * * *

UNITED STATES PATENT AND TRADEMARK OFFICE
CERTIFICATE OF CORRECTION

PATENT NO. : 11,189,813 B2  
APPLICATION NO. : 15/505642  
DATED : November 30, 2021  
INVENTOR(S) : Leiboff Page 1 of 1

It is certified that error appears in the above-identified patent and that said Letters Patent is hereby corrected as shown below:

In the Claims

Claim 1, Column 10, Line 40, delete "at least one channel".

Claim 3, Column 10, Line 57, delete "has".

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*